(12) United States Patent
Lueken et al.

(10) Patent No.: US 8,461,394 B2
(45) Date of Patent: Jun. 11, 2013

(54) PROCESS FOR PREPARING $C_5$ ALDEHYDE MIXTURES WITH A HIGH N-PENTANAL CONTENT

(75) Inventors: Hans-Gerd Lueken, Marl (DE); Dirk Fridag, Haltern am See (DE); Udo Lenz, Recklinghausen (DE); Hermann-Josef Schulte-Althoff, Haltern am See (DE); Klaus-Diether Wiese, Haltern am See (DE); Alfred Kaizik, Marl (DE); Patrick Muhlack, Recklinghausen (DE); Wilfried Bueschken, Haltern am See (DE); Frank Hoeper, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 172 days.

(21) Appl. No.: 12/995,800

(22) PCT Filed: Apr. 28, 2009

(86) PCT No.: PCT/EP2009/055133
§ 371 (c)(1),
(2), (4) Date: Feb. 18, 2011

(87) PCT Pub. No.: WO2009/146985
PCT Pub. Date: Dec. 10, 2009

(65) Prior Publication Data
US 2011/0130595 A1 Jun. 2, 2011

(30) Foreign Application Priority Data
Jun. 3, 2008 (DE) .................... 10 2008 002 187 U

(51) Int. Cl.
*C07C 45/50* (2006.01)

(52) U.S. Cl.
USPC .......................................... 568/454

(58) Field of Classification Search
USPC .......................................... 568/454
See application file for complete search history.

(56) References Cited

U.S. PATENT DOCUMENTS

| | | | |
|---|---|---|---|
| 4,668,651 A | 5/1987 | Billig et al. | |
| 7,193,116 B2 | 3/2007 | Moeller et al. | |
| 7,317,130 B2 | 1/2008 | Moller et al. | |
| 7,381,838 B2 | 6/2008 | Wiese et al. | |
| 2002/0111487 A1 | 8/2002 | Roettger et al. | |
| 2004/0138508 A1 | 7/2004 | Tinge et al. | |
| 2008/0188686 A1 | 8/2008 | Hess et al. | |
| 2010/0036143 A1 | 2/2010 | Selent et al. | |
| 2011/0130595 A1 | 6/2011 | Lueken et al. | |
| 2012/0190895 A1 | 7/2012 | Kaizik et al. | |

FOREIGN PATENT DOCUMENTS

| | | |
|---|---|---|
| EP | 1 201 675 | 5/2002 |
| WO | 2007 028660 | 3/2007 |
| WO | 2008 124468 | 10/2008 |

OTHER PUBLICATIONS

International Search Report issued Nov. 3, 2009 in PCT/EP09/055133 filed Apr. 28, 2009.
U.S. Appl. No. 13/256,116, filed Sep. 27, 2011, Kaizik, et al.
U.S. Appl. No. 13/386,523, filled Jan. 23, 2012, Grass, et al.
U.S. Appl. No. 13/703,925, filed Dec. 13, 2012, Franke, et al.

*Primary Examiner* — Sikarl Witherspoon
(74) *Attorney, Agent, or Firm* — Oblon, Spivak, McClelland, Maier & Neustadt, L.L.P.

(57) ABSTRACT

A process for preparing a $C_5$ aldehyde mixture from a hydrocarbon mixture comprising at least one linear butene by terminal hydroformylation under isomerizing conditions, using a catalyst system comprising rhodium, a bisphosphite ligand, and an amine.

18 Claims, 1 Drawing Sheet

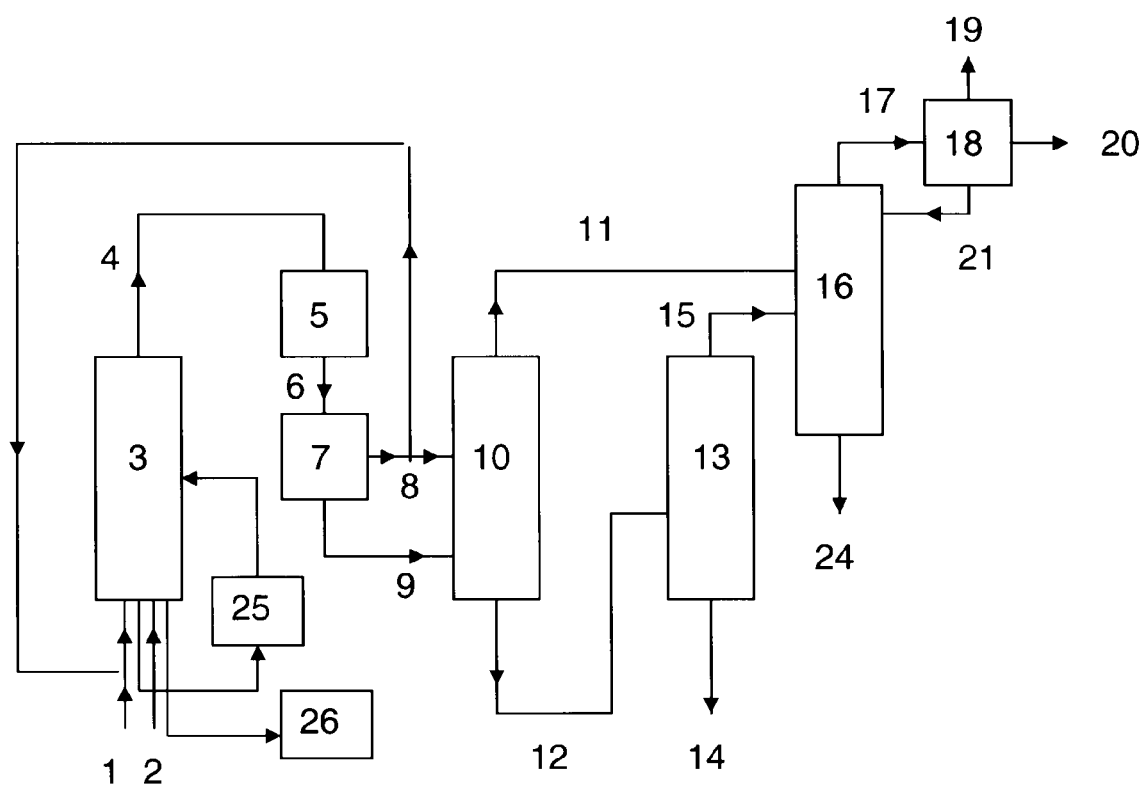

PROCESS FOR PREPARING C₅ ALDEHYDE MIXTURES WITH A HIGH N-PENTANAL CONTENT

The present invention relates to a process for preparing $C_5$ aldehyde mixtures with a high n-pentanal content from a hydrocarbon mixture comprising linear butenes. More particularly, the invention relates to the preparation of $C_5$ aldehyde mixtures with a ratio of n-pentanal to 2-methylbutanal of greater than 90:10 from a hydrocarbon mixture comprising linear butenes.

$C_5$ aldehydes are starting materials for obtaining pentanols, pentanoic acids and pentylamines. By aldol condensation and total hydrogenation of the aldol condensate, it is possible to obtain decanols therefrom, which are intermediates for the production of plasticizers, detergents and lubricants. By the aldol condensation thereof, hydrogenation of the olefinic double bond of the aldol condensate and subsequent oxidation of the aldehydic group, it is possible to obtain decanoic acids, which can be used, for example, to produce lubricants or detergents. In this field of use, it is important that the $C_5$ aldehydes consist very substantially exclusively of the linear n-pentanal compound, and the proportion of branched $C_5$ aldehydes, especially 2-methylbutanal, is at a minimum.

$C_5$ aldehydes can be obtained by hydroformylating unsaturated $C_4$ compounds. Corresponding industrially available starting materials are hydrocarbon mixtures which comprise 1-butene, the 2-butenes (Z and E) and isobutene. According to the position of the C—C double bond in the unsaturated $C_4$ compounds and depending on the reaction conditions, the hydroformylation thereof affords linear and branched $C_5$ aldehydes or $C_5$ aldehyde mixtures in different selectivity.

1-Butene can be hydroformylated to n-pentanal in more than 90% selectivity. The catalysts used for this purpose are usually complexes of rhodium and monophosphines. An example of a standard catalyst is a complex consisting of rhodium and triphenylphosphine. The reaction can be carried out in homogeneous phase, as described, for instance, in EP 0 562 451, or in heterogeneous phase, as described, for instance, in DE 026 27 354 or EP 0 562 451.

Optionally, the hydroformylation of the 1-olefins can be carried out in a polyphasic system, in which case reactant, product and synthesis gas are dispersed in a continuous catalyst phase, under high superficial velocities. Such processes are described, for example, in DE 199 25 384 A1 and DE 199 57 528 A1.

The selective preparation of n-pentanal from 2-butenes or from mixtures thereof is significantly more difficult. DE 101 08 474, DE 101 084 75, DE 101 084 76 and DE 102 252 82 describe the preparation of $C_5$ aldehyde mixtures by hydroformylating a mixture of linear butenes. What is common to the technical teachings of all of these documents is that a rhodium catalyst with a diphosphine ligand which has a xanthene structure is used in at least one hydroformylation step. This catalyst can hydroformylate 2-butenes under isomerizing conditions. The ratio of n-pentanal to 2-methylbutanal is at best 85:15. Documents DE 101 08 474 and DE 101 08 475 describe processes in which the hydroformylation is effected in two stages. In the first hydroformylation stage, using a catalyst consisting of rhodium and a monophosphine as the ligand, 1-butene is converted to n-pentanal in a selectivity of 90%. The unconverted butenes, principally 2-butenes, are converted in the second hydroformylation stage using the abovementioned rhodium/bisphosphine. Documents DE 101 08 476 and DE 102 25 282 describe one-stage hydroformylation processes.

Higher selectivities of n-pentanal in the hydroformylation of 2-butenes can be obtained when using a catalyst consisting of rhodium and bulky aromatic bisphosphites, as described, for example, in EP 0 213 639. However, the selectivity decreases significantly with time.

DE 10 2005 042464 specifies, for the hydroformylation of olefins, catalyst systems which comprise a complex consisting of rhodium and an organophosphorus compound and a sterically hindered secondary amine. These catalyst systems are notable for high long-term stability. They can be used for the hydroformylation of olefins having 3 to 16 carbon atoms. In the examples, only 1-octene was hydroformylated. Mixtures of a plurality of $C_9$ aldehydes were formed, but there are no statements about the isomer distribution thereof.

It was an object of the present invention to specify a process with which n-pentanal can be obtained in maximum selectivity from a hydrocarbon mixture comprising linear butenes.

It has now been found that a specific catalyst system consisting of rhodium and an organic bisphosphite and of a sterically hindered secondary amine brings about a selective hydroformylation of 2-butenes to n-pentanal and hence is particularly suitable in a process for preparing $C_5$ aldehyde mixtures with a high n-pentanal content from a hydrocarbon mixture comprising linear butenes. The catalyst system is a complex rhodium compound, which comprises at least one ligand of the formula I

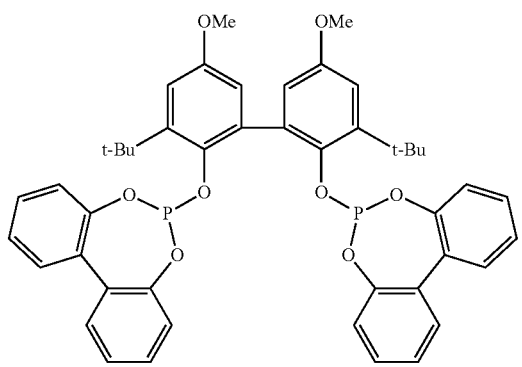

and at least one sterically hindered secondary amine of the general formula II

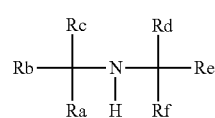

in which Ra, Rb, Rc, Rd, Re and Rf are identical or different hydrocarbon radicals which may also be joined to one another.

The present invention provides a process for preparing $C_5$ aldehyde mixtures from a hydrocarbon mixture comprising linear butenes by terminal hydroformylation under isomerizing conditions, using a catalyst system comprising rhodium, a bisphosphite ligand of the formula I and an amine of the formula II.

The catalyst system has the advantage that it is suitable for hydroformylating 2-butenes or mixtures of linear butenes with any ratio of 2-butenes to 1-butene in a selectivity of more than 90% to n-pentanal. In addition, the loss of rhodium and bisphosphite is so low that there is an economic advantage compared to other catalyst systems. In addition, it is advantageous that the butene hydroformylation can be carried out with this catalyst system in existing plants for propene hydroformylation.

Feedstocks

Feedstocks for the process according to the invention are linear butenes and any mixtures thereof. These mixtures may contain up to 5% by mass of isobutene, based on the $C_4$ olefin fraction. Preference is given to using mixtures which contain less than 1% by mass of isobutene, especially less than 0.1% by mass of isobutene. In the feedstock mixtures, saturated hydrocarbons having 1 to 7 carbon atoms, especially having 4 carbon atoms, and benzene and toluene may be present. Preference is given to using $C_4$ hydrocarbon mixtures, especially those in which the mass ratio of the sum of the two 2-butenes to 1-butene is greater than 2:1, preferably greater than 5:1 and most preferably greater than 10:1.

Feedstocks for the process according to the invention may be mixtures which are obtained in the dehydrogenation of n-butane and from which by-products and polyunsaturated compounds have been removed.

Other feedstocks are low-isobutene fractions which are obtained in the workup of $C_4$ cuts from hydrocrackers, FC crackers or steamcrackers. One example thereof is the so-called raffinate II, which is obtained from a $C_4$ cut by removal of the polyunsaturated compounds, such as principally butadiene, and isobutene. It contains 1-butene, the two 2-butenes, n-butane and isobutane. When isobutane and a portion of the 1-butene are removed, raffinate III is obtained. Raffinate II and raffinate III are suitable feedstocks. Raffinate II and raffinate III can be utilized for the preparation of butene oligomers. The remaining residual streams, consisting of n-butane, linear butenes, principally 2-butenes and optionally isobutane, can likewise be used in the process according to the invention.

The synthesis gas used has a molar ratio of hydrogen to carbon monoxide in the range from 2:1 to 1:2, especially in the range from 1.1:0.9 to 0.9:1.1.

Before use, the synthesis gas used is preferably purified by processes known per se. It contains preferably less than 1 ppm by mass of sulphur compounds (calculated as elemental sulphur) and less than 1 ppm by mass of oxygen. Optionally, the synthesis gas under reaction conditions may comprise inert gases, for example methane or nitrogen.

Catalyst System

In the process according to the invention, a catalyst system which consists of a complex rhodium compound, which comprises at least one ligand of the formula I, and at least of one sterically hindered secondary amine is used.

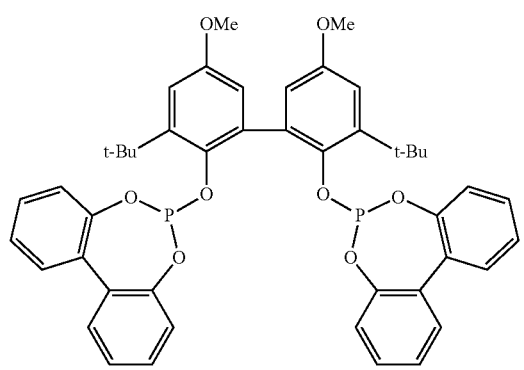

The sterically hindered secondary amines used are compounds of the general formula II

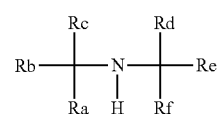

where Ra, Rb, Rc, Rd, Re and Rf are identical or different hydrocarbon radicals which may also be joined to one another.

In the process according to the invention, preference is given to using secondary amines which have a 2,2,6,6-tetramethylpiperidine unit IIa

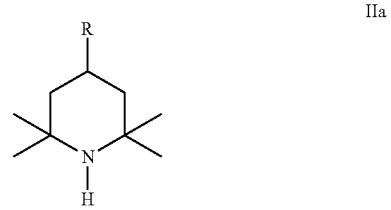

where R is H, such as 2,2,6,6-tetramethylpiperidine itself, an organic radical, a hydroxyl group or a halogen.

The organic R radical may also be an organic radical bonded to the 2,2,6,6-tetramethylpiperidine structural unit via a heteroatom, for example, an oxygen atom. More particularly, the organic radical may have polymeric structures or be an organic radical having 1 to 50 carbon atoms and optionally heteroatoms. More preferably, the organic radical has carbonyl groups, such as keto, ester or acid amide groups. The organic radical optionally having heteroatoms may especially be a substituted or unsubstituted, aliphatic, alicyclic, aliphatic-alicyclic, heterocyclic, aliphatic-heterocyclic, aromatic, aromatic-aromatic or aliphatic-aromatic hydrocarbon radical having 1 to 50 carbon atoms, where the substituted hydrocarbon radicals may have substituents selected from primary, secondary or tertiary alkyl groups, alicyclic groups, aromatic groups, $-N(R^1)_2$, $-NHR^1$, $-NH_2$, fluorine, chlorine, bromine, iodine, $-CN$, $-C(O)-R^1$, $-C(O)H$ or $-C(O)O-R^1$, $-CF_3$, $-O-R^1$, $-C(O)N-R^1$, $-OC(O)-R^1$ and/or $-Si(R^1)_3$, where $R^1$ is a monovalent hydrocarbon radical, preferably having 1 to 20 carbon atoms. When a plurality of hydrocarbon radicals $R^1$ are present, they may be the same or different. The substituents are preferably restricted to those which have no influence on the reaction itself. Particularly preferred substituents may be selected from the halogens, for example, chlorine, bromine or iodine, the alkyl radicals, for example, methyl, ethyl, propyl, isopropyl, butyl, sec-butyl, t-butyl, neopentyl, sec-amyl, t-amyl, isooctyl, t-octyl, 2-ethylhexyl, isononyl, isodecyl or octadecyl, the aryl radicals, for example phenyl, naphthyl or anthracyl, the alkylaryl radicals, for example tolyl, xylyl, dimethylphenyl, diethylphenyl, trimethylphenyl, triethylphenyl or p-alkylphenyl, the aralkyl radicals, for example benzyl or phenylethyl, the alicyclic radicals, for example cyclopentyl, cyclohexyl, cyclooctyl, cyclohexylethyl or 1-methylcyclohexyl, the alkoxy radicals, for example methoxy, ethoxy, propoxy, butoxy or pentoxy, the aryloxy radicals, for example phenoxy or naphthoxy, $-OC(O)R^1$ or $-C(O)R^1$, for example acetyl, propionyl, trimethylacetoxy, triethylacetoxy or triphenylacetoxy, and the silyl radicals having three hydrocarbon radicals —Si(R¹)₃, for example trimethylsilyl, triethylsilyl or triphenylsilyl. Particular preference is given to compounds of the formula IIa, which, as R radicals, have those which contain a 2,2,6,6-tetramethylpiperidine radical and optionally a further —N(R¹)₂, —NHR¹ and/or —NH₂ group.

The secondary amines which have a structural unit of the formula II used may most preferably be the compounds listed below with the structural formulae IIb to IIg or derivatives thereof.

IIb
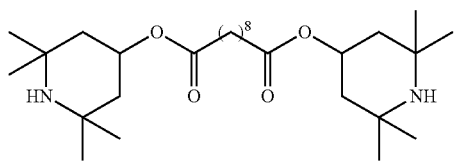

IIc
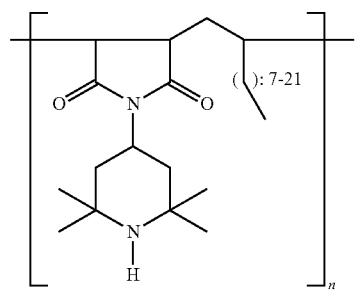

where n=1 to 20, preferably 1 to 10

IId
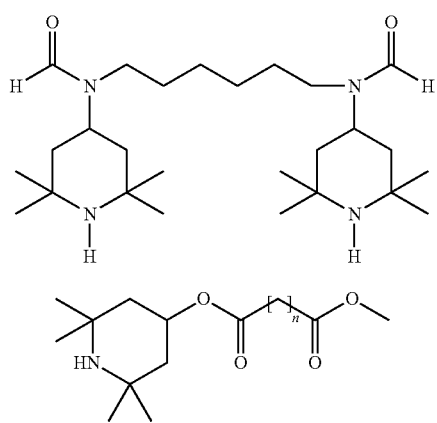

IIe where n=1 to 12, preferably 8

IIf
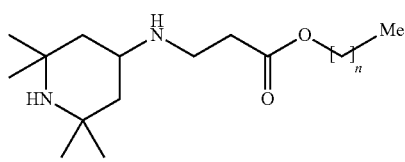

where n=1 to 17, preferably 13

IIg
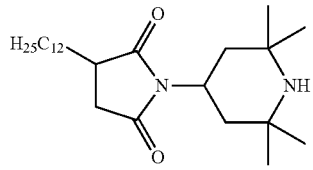

It is also possible to use mixtures comprising two or more sterically hindered amines. In particular, in the process according to the invention it is possible with preference to use the amine of the formula IIb, di-4(2,2,6,6-tetramethylpiperidinyl)sebacate.

In the catalyst system, the three components, rhodium, bisphosphite of the formula I and sterically hindered amine II, are present in particular molar ratios.

The molar ratio of rhodium to bisphosphite I is within the range from 1:1 to 1:100, especially 1:1 to 1:20, very particularly within the range from 1:2 to 1:5.

The molar ratio of bisphosphite I to sterically hindered secondary amine II is within the range from 0.1:10 to 10:1, especially in the range from 5:10 to 10:5, very particularly in the range from 0.8:1 to 1:0.8.

The concentration of the rhodium in the reaction mixture is within the range from 1 to 1000 ppm by mass, especially within the range from 20 to 300 ppm by mass, very particularly within the range from 40 to 150 ppm by mass.

The rhodium catalyst can be introduced into the process as an active complex. The active complex is preferably prepared in the hydroformylation reactor under hydroformylation conditions in the presence of the bisphosphite I from stable, easily storable rhodium compounds. Suitable rhodium compounds for this purpose are, for example, rhodium(II) and rhodium(III) salts, such as rhodium(III) chloride, rhodium(III) nitrate, rhodium(III) sulphate, potassium rhodium sulphate, rhodium(II) and/or rhodium(III) carboxylate, rhodium(II) and rhodium(III) acetate, rhodium(II) octanoate, rhodium(II) nonanoate, rhodium(III) oxide, salts of rhodium(III) acid, trisammoniohexachlororhodate(III). Additionally suitable are rhodium complexes, such as rhodium biscarbonylacetylacetonate, acetylacetonatobisethylenerhodium(I). Particularly suitable are rhodium acetate, rhodium octanoate and rhodium nonanoate.

The catalyst system, consisting of at least one rhodium complex, ligand, amine and other rhodium compounds, is preferably dissolved in the hydroformylation mixture, consisting of feed hydrocarbon mixture and products (C₅ aldehydes, C₅ alcohols, heavy fraction). Optionally, it is additionally possible to use a solvent, for example, toluene, ester derivatives of 2,2,4-trimethylpentane-1,3-diol (Texanol®), eutectic mixture of biphenyl and diphenyl ether (Diphyl®), heavy fraction, phthalates, such as di(2-ethylhexyl) phthalate or dinonyl phthalate, or esters of 1,2-cyclohexanoic acids or esters of benzoic acid, for example, isononyl benzoate.

Process Procedure

In the process according to the invention, the hydroformylation is performed at temperatures within the range from 70 to 150° C., preferably from 80 to 130° C., especially within the range from 100 to 120° C.

The reaction pressure is 1 to 20 MPa, preferably 1.0 to 3.5 MPa and especially 1.5 to 2.1 MPa.

The hydroformylation is preferably carried out continuously. The reaction vessels used may, for example, be bubble column reactors or stirred tanks.

The hydroformylation products can be removed by distillative workup of the liquid hydroformylation mixture. The gaseous phase drawn off from the reactor is partially condensed. The component which is still gaseous is for the most part recycled into the reaction system. Subsequently, the liquid products are separated by distillation.

Preferably, in the process according to the invention, the reaction products, especially the $C_5$ aldehydes, are discharged from the reactor with reaction gas. The reaction gas essentially consists of unconverted synthesis gas, unconverted reactants and $C_5$ aldehydes, and the reactant may also contain an inert component of saturated hydrocarbons. To this end, 500 to 9000 $m^3$ (STP) of reaction gas per t of feedstock are introduced with the aid of at least one nozzle into the liquid phase in the reactor. The relative amount of the reaction gas depends on the liquid level in the reactor, which should be 20 to 80% of the reactor height. This means that the amount of reaction gas is increased when the liquid level is high and reduced when the level is low.

The reaction gas leaving the reactor, which is laden with reactant and products, is passed through a demister, in which the liquid droplets present in the gas stream are separated out. The liquid obtained is passed back into the reactor. This apparatus allows the discharge of catalyst with the gas phase to be minimized. Products and reactants are condensed out of the gas mixture and the synthesis gas, optionally after discharge of a portion, is recycled into the reactor. The condensate is separated into products and reactants in one or more columns.

When the reactant used is a hydrocarbon mixture which consists virtually only of n-butane and linear butenes, especially 2-butenes, the procedure is preferably in the following manner, which is illustrated with reference to a block diagram of a plant in which the process according to the invention can be performed (FIG. 1).

Synthesis gas (1), a portion of the gas phase removed (8) and reactant (2) are introduced into the hydroformylation reactor (3) in which a liquid phase is present. A gaseous stream (4), consisting of synthesis gas, reactant and products, is drawn off, partly condensed in the apparatus (5) and separated into a liquid phase (9) and a gas phase (8) in the separating vessel (7). After compression, a portion of the gas phase (8) is recycled into the reactor (3). The other portion of stream (8) and the liquid phase (9) are introduced into the distillation column (10), in which a top product consisting of $C_4$ hydrocarbons and synthesis gas is removed. The bottom product (12) is separated in the column (13) into a bottom product (14) which comprises the $C_5$ aldehydes formed and other products, and a top product (15). The two top products (11) and (15) are separated in the column (16). The bottom product obtained is a $C_4$ hydrocarbon mixture. The top product (17) is partly condensed and separated in the separation vessel (18) into a gas phase (19), principally synthesis gas, a water phase (20) and a liquid $C_4$ hydrocarbon phase (21), which is recycled into the column (16).

The gas phase (19) can optionally be recycled partly into the reactor (3). It may likewise be appropriate to recycle a portion of the hydrocarbon stream (24) into the reactor (3). Optionally, the apparatuses (5) and (7) may consist of one apparatus. A further option is to replace the columns (10) and (13) with one column. Optionally, a portion of the reactor contents is circulated through a filter (25) under reaction pressure, in order to remove insoluble conversion products of the bisphosphite ligand I from the reaction system.

In order to prevent synthesis gas depletion in the reaction solution, the residence time in the filtration unit has to be limited. The residence time in the filtration unit is in the range of 5-10 minutes, especially in the range of 2-5 minutes, very particularly below 2 minutes.

As a further option, the feed to this filtration unit (25) is cooled. This aims to lower the temperature of the feed by 5-20° C., especially to lower the temperature by 20-30° C., very particularly to lower the temperature by 30-40° C., below the reaction temperature.

The filtration can be effected continuously or batchwise.

The individual workup steps of the hydroformylation mixture will be described in more detail hereinafter.

Removal of Entrained Liquid Droplets

The gaseous reaction effluent comprises ultrafine liquid droplets which comprise the catalyst system. To minimize the catalyst losses, especially of the rhodium, the droplets are removed from the gas phase by means of an aerosol separator. The aerosol separators used are vessels with internals, for example demisters, cyclone separators, lamellar separators, random packings, filter cartridges.

The aerosol separator is preferably operated at reactor pressure and reactor temperature. It is designed to be sufficiently large that more than 99.9%, especially more than 99.99% of the entrained liquid is separated out. The liquid removed is passed back into the reactor. In the gas phase leaving the aerosol separator, the rhodium content is below the detection limit of 0.1 ppm Condensation and Phase Separation The partial condensation of the gaseous reaction mixture can be effected in customary industrial condensers, for example, tube bundle or plate heat exchangers. The condensation is carried out within the temperature range from 3 to 90° C., especially within the range from 15 to 60° C. The coolant used to remove the heat of condensation may, for example, be air, water or cooling brine. The pressure is lower than that in the hydroformylation reactor and lower than the pressure in the downstream column.

After the partial condensation, the liquid phase is separated from the gas phase in a downstream vessel.

The gas phase comprises the majority of the excess synthesis gas. In addition, according to the partial pressures of the components, it comprises further substances in the liquid phase. The gas phase comprises, as well as synthesis gas, principally $C_4$ hydrocarbons and, to a lesser degree, $C_5$ aldehydes.

The gas phase is passed to the suction side of a gas compressor. The majority (approx. 99%) of the gas phase is recycled into the hydroformylation reactor. The other portion, downstream of the compressor, is fed into a separation column (10). It is appropriate, in order to protect the compressor, to strip out liquid droplets present in the gas, for example, using an aerosol separator.

The liquid phase comprises the majority of the products, reactants and dissolved synthesis gas.

Example of the composition of the liquid phase:
butane 50 to 60%, butene 3 to 10%, 30 to 40% pentanal, 2 to 8% 2-methylbutanal, 0.5 to 2% CO, <1% water. It is introduced into column (10).

Distillative Workup in Columns (10), (13), (16)

The substance mixture is preferably separated in three columns. These columns can be provided with internals which are, for example, composed of trays, rotating internals, random packings and/or structured packings.

In the case of the column trays, it is possible to use, for example, the following types:

Trays with bores or slots in the tray plate.
Trays with necks or chimneys which are covered by caps or hoods.
Trays with bores in the tray plate, which are covered by mobile valves.
Trays with special constructions.

In columns with rotating internals, the reflux can, for example, be sprayed by rotating funnels or spread out with the aid of a rotor as a film on a heated tube wall.

In the process according to the invention, as already stated, it is possible to use columns which have random beds of various random packings. The random packings may consist of almost all materials, more particularly of steel, stainless steel, copper, carbon, stoneware, porcelain, glass or plastics, and may have a wide variety of different forms, especially the form of spheres, rings with smooth or profiled surfaces, rings with internal elements or wall penetrations, wire mesh rings, saddles and spirals.

Packings with regular/structured geometry may consist, for example, of metal sheets or fabrics. Examples of such packings are Sulzer BX fabric packings made of metal or plastic, Sulzer Mellapak lamellar packings made of sheet metal, Sulzer high-performance packings such as Mella-pakPlus, structured packings from Sulzer (Optiflow), Montz (BSH) and Kühni (Rombopak).

Preliminary Separation in Column (10)

In the column (10), the portion of the gas phase (8), which is not recycled into the reactor, and the liquid phase (9) are separated into a bottom product (12), consisting of products and a small proportion of $C_4$ hydrocarbons, and a top product (11) which comprises synthesis gas and the majority of the $C_4$ hydrocarbons but no products.

The column (10) has 10 to 30 theoretical plates, especially 25 to 35 theoretical plates. The liquid phase is introduced to the 15th to 25th theoretical plate, especially to the 20th to 22nd theoretical plate. The gas phase (8) is introduced to the 15th to 25th theoretical plate, especially to the 20th to 22nd theoretical plate. (Trays numbered 1 at the top→25 at the bottom).

The feed streams have temperatures within the range from 10 to 125° C., especially within the range from 40 to 100° C., especially within the range from 80 to 90° C.

Column (10) is preferably operated at a pressure between 1 and 2 MPa, especially at a pressure within the range from 1.6 to 1.8 MPa.

The top temperature and bottom temperature are pressure-dependent. At a pressure of 1.6 to 1.8 MPa, the top temperature is between 95 and 105° C. and the bottom temperature between 125 and 140° C.

The reflux ratio based on the components condensable under these conditions ($C_4$ hydrocarbons) is within the range from 0.5 to 3, especially within the range from 1 to 2.

Separation in Column (13)

In column (13) the remaining $C_4$ hydrocarbons are removed as the top product from the bottom product (12).

The column (13) has 5 to 20 theoretical plates, especially 8 to 15 theoretical plates. The liquid phase (12) is introduced to the 5th to 12th theoretical plate, especially to the 6th to 9th theoretical plate.

Column (13) is preferably operated at a pressure between 0.1 and 0.8 MPa, especially at a pressure within the range from 0.4 MPa.

The top temperature and bottom temperature are pressure-dependent. At a pressure of 0.4 MPa, the top temperature is 45° C. and the bottom temperature is 160° C.

The reflux ratio is within the range from 0.5 to 3, especially within the range from 1 to 2.

The bottom product (14) obtained is a mixture which consists of $C_5$ aldehydes to an extent of more than 95%, especially more than 97%, very particularly more than 98%. In addition, this mixture may comprise pentanols and high boilers formed from the pentanals. The content of n-pentanal is at least 90%.

Separation in Column (16)

Column (16) serves to separate synthesis gas, $C_4$ hydrocarbons and water, which has been introduced by the reactants and/or has formed through side reactions, for example, aldol condensation of aldehydes.

The column (16) has 5 to 25 theoretical plates, especially 10 to 20 theoretical plates. The top products (11) and (15) of the two columns (10) and (13) are introduced to the 1st to 5th theoretical plate, especially to the 1st to 3rd theoretical plate. The feed temperature is preferably between 40 and 100° C.

The column (16) is preferably operated at 1.5 MPa. The bottom temperature is 100° C., the top temperature approx. 93° C.

The top product (17) is condensed and, after cooling to about 5° C., separated in the separating vessel (18) into a gas phase (19), a water phase (20) and an organic phase (21), which is introduced into column (16) as reflux.

Alternatively, stream (17) can be combined with the top products (11) and (15). After cooling to 5° C., this stream is separated into a gas phase (19a), a water phase (20a) and an organic phase, which is introduced into column (16) as reflux to the top.

Use of Streams (19), (20) and (24)

The gas phase (19) consists of synthesis gas, inert gas, for example nitrogen or carbon dioxide, and steam. Depending on the inert gas content, it may be recycled (3) partly into the hydroformylation reactor. The other portion, preferably the entirety, can be utilized thermally or physically. The gas removed can be used, for example, as heating gas. Another utilization of the gas is, for example, to obtain hydrogen, for example by conversion.

The water removed (20) is discarded or optionally used as process water.

The hydrocarbon mixture (24) consists principally of butane. The butane content is dependent on the butane content in the reactant and conversion of the linear butenes. The butane content is preferably greater than 80%, especially greater than 90%. In addition, stream (24) may comprise small amounts of products, especially n-pentanal. The content of products is less than 10 ppm by mass, especially less than 1 ppm by mass.

A portion of stream (24) can be recycled into the hydroformylation reactor (3), with the proviso that the overall hydrocarbon mixture (sum of fresh reactant (2), hydrocarbons from the partly recycled streams (8) and (24)) introduced into the hydroformylation reactor (3) has a content of linear butenes of greater than 15% by mass, especially of greater than 20, very particularly greater than 25. This stream is not shown in FIG. 1.

Stream (24) can be used for heating purposes. Without further workup, it can be used to prepare acetylene or synthesis gas. After hydrogenation of the butenes, it can be worked up to pure butane which finds use as a propellant for aerosols. In addition, pure n-butane is used to prepare maleic anhydride.

Use of the Target Product (14)

The bottom product (14), which, as already described, consists of $C_5$ aldehydes, small amounts of $C_5$ alcohols and less than 1% of high boilers, can be used as such, processed further or separated by distillation. Distillation can provide pure n-pentanal (b.p. 102-103° C.), pure 2-methylbutanal (b.p. 91-92° C.), 2-methylbutanol (b.p. 129° C.) and n-pentanol (b.p. 138° C.).

The $C_5$ aldehydes can be hydrogenated to the corresponding alcohols. Their oxidation affords the corresponding carboxylic acids.

By aldol condensation of the $C_5$ aldehydes, it is possible to prepare a decenal mixture. To this end, the reactant used may additionally be a $C_s$ aldehyde stream which originates from an alternative preparation process, for example, that of the parallel application "Verfahren zur Abtrennung von 1-Buten aus $C_4$-haltigen Kohlenwasserstoffströmen durch Hydroformylierung" [Process for removing 1-butene from $C_4$-containing hydrocarbon streams by hydroformylation]. The aldol condensation can be carried out by processes known per se. More particularly it is effected as described in DE 199 57 522:

The decenal mixture is hydrogenated to a decanol mixture, a sought-after plasticizer alcohol. The hydrogenation is likewise effected by processes known per se, for example within the temperature range from 170 to 200° C. at a pressure of 15 to 30 bar over a supported catalyst which comprises nickel, copper and chromium as active components.

Preference is given to preparing a decanol mixture with a 2-propylheptanol content of at least 90%. At an n-pentanal/2-methylbutanal ratio of less than 90 to 10, a portion of the 2-methylbutanal is then removed before the aldol condensation.

In addition, a decanoic acid mixture with a high proportion of 2-propylheptanoic acid can be obtained from the bottom product (14) by aldol condensation, selective hydrogenation of the condensate to decanal and subsequent oxidation.

Workup of the Liquid Reactor Phase

After the production phase has ended, the content of butane, butenes and aldehydes in the reaction mixture can be reduced with the aid of the circulation gas. Subsequently, the reactor contents can be concentrated by means of a thin-film evaporator. The ratio of distillate and bottoms should be 2:1, preferably 5:1 and especially 7:1 or higher. The bottom stream must still be free-flowing at room temperature and must not have any precipitates whatsoever. At least 90% of the rhodium present in the feed stream is present in the bottom product. The rhodium-containing bottoms processed in this way can be sent to a rhodium recovery step. The distillate phase can be sent to further physical utilization and may, for example, find use as a high-boiling solvent, as a feedstock for synthesis gas production, as a fuel used to produce sulphuric acid or in the fuels sector.

Optionally, the liquid reactor phase can be discharged from the reactor in the course of operation and sent to the above-described workup.

The examples which follow are intended to illustrate the invention without restricting the scope of application which is evident from the description and the claims.

EXAMPLES

A hydroformylation of butene/butane mixtures was carried out in a continuous pilot plant.

This pilot plant consisted of a pressurized reactor with a capacity of 20 liters and a downstream condenser and phase separation vessel (gas/liquid) for the gas phase originating from the reactor, and also a circulation gas compressor which recycles the gas phase from the phase separation vessel back down into the reaction zone. A portion of this circulation gas is conducted out of the reaction system as offgas after the phase separation.

In order to achieve optimal gas distribution in the reactor system, a manifold containing bores was installed here.

By means of installed heating and cooling apparatus, it was possible to control the temperature of the reactor.

Before the hydroformylation the reactor system was purged with nitrogen to free it of oxygen. Subsequently, the reactor was filled with 12 liters of catalyst solution. This catalyst solution was composed of 12 kg of a eutectic mixture of biphenyl and diphenyl ether (Diphyl®, heat carrier oil from Lanxess), 3 g of Rh(acac)(CO)$_2$, 36 g of bisphosphite ligand I, 67.5 g of amine IIb, and had been mixed beforehand in a vessel. The eutectic mixture of biphenyl and diphenyl ether (Diphyl®) had been stripped beforehand with nitrogen in order to remove oxygen and water from the heat carrier oil.

Subsequently, the reactor system was purged with synthesis gas to free it of nitrogen. Once the nitrogen content had fallen <10% by volume, the reactor system was pressurized to 1.0 MPa with synthesis gas and then heated to 120° C. On attainment of the operating temperature the reactor system was brought to reaction pressure 1.7 MPa with synthesis gas.

Thereafter, the addition of the starting materials was commenced. The butenes containing mixture was conducted through an evaporator in order to conduct it into the circulation gas in gaseous form.

The following throughputs were established:
0.3 kg/h of a mixture containing 35% 2-butenes and n-butane and 1-butene concentrations of approx. 1%, 75 l (STP)/h synthesis gas (50% by volume of $H_2$ and 50% by volume of CO).

For the daily dosage of the bisphosphite ligand I and amine IIb, a 1.4% solution of the bisphosphite ligand I in n-pentanal was made up, which had been freed of residual $C_4$ hydrocarbons (<3%) beforehand by stripping with nitrogen. The amine IIb was used in a threefold molar excess relative to the bisphosphite ligand I. To better stabilize this solution, the amine IIb was added to the solution before the bisphosphite ligand I.

After approx. 1000 h, a steady state was attained. The reaction products were removed continuously from the reactor via the cycle gas stream and condensed partially in the condenser at 50° C. The condensed phase was conducted continuously out of the phase separation vessel. To determine the conversion, samples were taken from the cycle gas upstream and downstream of the reactor. A daily dosage of 100 g of the before mentioned catalyst solution allowed the conversion and the regioselectivity to be kept constant.

To determine the reactor contents, samples were taken from the reactor and studied by means of liquid chromatography (HPLC).

Under the selected reaction conditions, butene conversions of about 65-70% were achieved. The percentage distribution between n-pentanal and 2-methylbutanal, i.e. n/iso selectivity was 95% to 5%.

In the steady-state phase of the experiment, no rhodium degradation was recorded.

After the end of the test, the reactor was decompressed and the catalyst solution was analysed. A precipitate was found in the reactor.

An analysis of this precipitate showed that it consisted of phosphorus-containing conversion products of the bisphosphite ligand I and the amine IIb used.

No caking of this precipitate whatsoever was found in the reactor vessel.

A portion of the reactor content was, after removal of the precipitate, concentrated to 13% based on the starting material at 1.2 KPa abs. and bottom temperature 220° C. The resulting residue from the bottoms was still free-flowing and no precipitate was found.

A rhodium analysis showed that all of the rhodium from the starting material was present in this bottom residue.

The invention claimed is:

1. A process for preparing a $C_5$ aldehyde mixture from a hydrocarbon mixture comprising at least one linear butene, the process comprising terminally hydroformylating the hydrocarbon mixture under isomerizing conditions in a reaction mixture comprising a catalyst system comprising:
   rhodium;
   a bisphosphite ligand of formula (I):

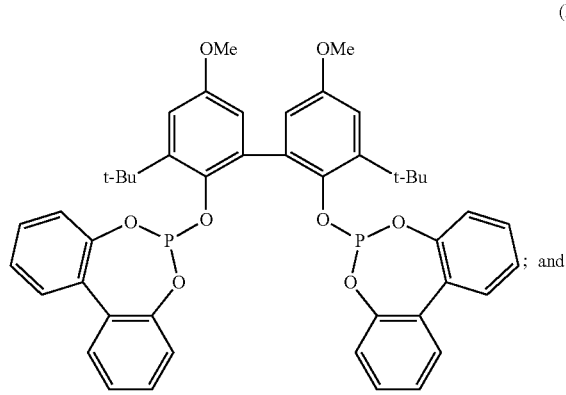

an amine of formula (II):

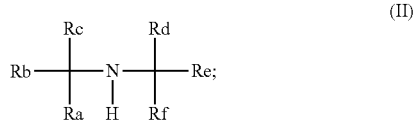

to form a C-5 aldehyde mixture, wherein:
   the hydrocarbon mixture comprises a residual content of 1-butene, in relation to isomeric 2-butenes, of less than 1:10;
   Ra, Rb, Rc, Rd, Re and Rf are identical or different hydrocarbon radicals optionally joined to one another; and
   the hydrocarbon mixture is hydroformylated with an n/iso selectivity of at least 90%.

2. The process according to claim 1, wherein the hydrocarbon mixture comprises up to 5% by mass, based on a $C_4$ olefin fraction, of isobutene.

3. The process according to claim 1, wherein a molar ratio of rhodium to the bisphosphite ligand is in a range from 1:2 to 1:5.

4. The process according to claim 1, wherein a molar ratio of the bisphosphite ligand to the amine is in a range of 0.1:10 to 10:1.

5. The process according to claim 1, wherein a concentration of the rhodium in the reaction mixture is 1 ppm by mass up to 1000 ppm by mass based on a total weight of the reaction mixture.

6. The process according to claim 1, wherein reaction is carried out within a temperature range from 70 to 150° C.

7. The process according to claim 1, wherein reaction is carried out within a pressure range from 1 to 20 MPa.

8. The process according to claim 1, wherein the process occurs continuously.

9. The process according to claim 1, further comprising removing precipitated reaction products from a feed, comprising a reaction solution and the precipitated reaction products, from a reactor circulation system by filtration under reaction pressure.

10. The process according to claim 9, wherein a residence time of the reaction solution during the filtration is less than 5 minutes.

11. The process according to claim 9, wherein a temperature of the feed to the filtration is within a range between 5 and 40° C. below reaction temperature.

12. The process according to claim 9, wherein the filtration occurs continuously.

13. The process according to claim 1, further comprising separating the C-5 mixture into $C_5$ aldehydes, synthesis gas, hydrocarbons, and a rhodium-comprising residue.

14. The process according to claim 2, wherein a molar ratio of rhodium to the bisphosphite ligand is in a range from 1:2 to 1:5.

15. The process according to claim 2, wherein a molar ratio of the bisphosphite ligand to the amine is in a range of 0.1:10 to 10:1.

16. The process of claim 1, wherein the reaction mixture further comprises a synthesis gas having a molar ratio of hydrogen to carbon monoxide in the range of 2:1 to 1:2.

17. The process of claim 1, wherein at least 90% of the rhodium is present in a bottom product at the end of reaction.

18. The process of claim 1, wherein the reaction mixture further comprises at least one solvent selected from the group consisting of an ester derivative of 2,2,4-trimethylpentane-1,3-diol, a eutectic mixture of biphenyl and diphenyl ether, a phthalate, an ester of 1,2-cyclohexanoic acid, and an ester of benzoic acid.

\* \* \* \* \*